(12) United States Patent
Donoghue et al.

(10) Patent No.: US 12,150,901 B2
(45) Date of Patent: Nov. 26, 2024

(54) DARKENING FILTER COMPRISING A NON-UNIFORM PATTERN OF SWITCHABLE SHUTTERS

(71) Applicant: 3M INNOVATIVE PROPERTIES COMPANY, St. Paul, MN (US)

(72) Inventors: Claire R. Donoghue, Twyford (GB); Britton G. Billingsley, St. Paul, MN (US); Kristina M. Magnusson, Djurmo (SE)

(73) Assignee: 3M Innovative Properties Company, St. Paul, MN (US)

( * ) Notice: Subject to any disclaimer, the term of this patent is extended or adjusted under 35 U.S.C. 154(b) by 437 days.

(21) Appl. No.: 17/595,277

(22) PCT Filed: May 19, 2020

(86) PCT No.: PCT/IB2020/054723
§ 371 (c)(1),
(2) Date: Nov. 12, 2021

(87) PCT Pub. No.: WO2020/234759
PCT Pub. Date: Nov. 26, 2020

(65) Prior Publication Data
US 2022/0249290 A1 Aug. 11, 2022

(30) Foreign Application Priority Data
May 23, 2019 (EP) ..................................... 19176137

(51) Int. Cl.
*A61F 9/06* (2006.01)
*B60J 3/04* (2006.01)
(Continued)

(52) U.S. Cl.
CPC ................. *A61F 9/067* (2013.01); *B60J 3/04* (2013.01); *E06B 9/24* (2013.01); *G02F 1/0128* (2013.01);
(Continued)

(58) Field of Classification Search
CPC .. A61F 9/067; A61F 2250/0053; A61F 9/023; B60J 3/04; E06B 9/24;
(Continued)

(56) References Cited

U.S. PATENT DOCUMENTS 4,240,709 A 12/1980 Hornell
4,968,127 A 11/1990 Russell
(Continued)

FOREIGN PATENT DOCUMENTS

EP 2428836 3/2012
WO WO 1997-022904 6/1997
(Continued)

OTHER PUBLICATIONS

Extended European Search Report for EP Application No. 19176137.8, mailed on Dec. 10, 2019, 2 pages.
(Continued)

*Primary Examiner* — Mariam Qureshi

(57) ABSTRACT

The present disclosure relates to darkening filters 10, 10' which are suitable for selectively darkening an optically transmissive window 20 for protection from light, in particular from high intensity light. The darkening filter 10, 10' is mounted in a forward-facing optically transmissive window 20 and comprises a non-uniform pattern 30 of switchable shutters 32 capable of being switching to at least a dark state and a light state by a shutter control system 40. The present disclosure also relates to a method of operating such darkening filters 10, 10'. The present disclosure furthermore relates to vision-protective headgears 100, 100', welding
(Continued)

shields 110 and panes 120 comprising the darkening filters 10, 10' according to the present disclosure.

11 Claims, 6 Drawing Sheets

(51) Int. Cl.
*E06B 9/24* (2006.01)
*G02F 1/01* (2006.01)

(52) U.S. Cl.
CPC ............... *A61F 2250/0053* (2013.01); *E06B 2009/2405* (2013.01); *E06B 2009/2464* (2013.01)

(58) Field of Classification Search
CPC ..... E06B 2009/2405; E06B 2009/2464; G02F 1/0128; G02F 1/134336
See application file for complete search history.

(56) References Cited

U.S. PATENT DOCUMENTS

| | | | |
|---|---|---|---|
| 5,015,086 A | 5/1991 | Okaue | |
| 5,076,669 A | 12/1991 | Black | |
| 5,114,218 A | 5/1992 | Black | |
| 5,184,156 A | 2/1993 | Black | |
| 5,276,539 A | 1/1994 | Humphrey | |
| 5,298,732 A | 3/1994 | Chen | |
| 5,305,012 A | 4/1994 | Faris | |
| 5,382,986 A | 1/1995 | Black | |
| 5,608,567 A | 3/1997 | Grupp | |
| 5,671,035 A | 9/1997 | Barnes | |
| 5,841,507 A | 11/1998 | Barnes | |
| 5,959,705 A | 9/1999 | Fergason | |
| 6,169,526 B1 | 1/2001 | Simpson | |
| 6,170,947 B1 | 1/2001 | Colles | |
| 6,760,080 B1 | 7/2004 | Moddel | |
| 6,786,610 B2 | 9/2004 | Faris | |
| 6,864,473 B2 | 3/2005 | Chretien | |
| 6,992,731 B1 | 1/2006 | Morris | |
| 7,008,055 B2 | 3/2006 | McLear | |
| 7,585,068 B2 | 9/2009 | Mullin | |
| 7,874,666 B2 | 1/2011 | Xu | |
| 7,970,172 B1 | 6/2011 | Hendrickson | |
| 8,081,262 B1 | 12/2011 | Perez | |
| 8,143,563 B2 | 3/2012 | Broude | |
| 8,177,357 B2 | 5/2012 | Kamiya | |
| 8,791,990 B2 | 7/2014 | Luber | |
| 8,797,236 B2 | 8/2014 | Seo | |
| 9,057,944 B2 | 6/2015 | Sugiyama | |
| 9,405,135 B2 | 8/2016 | Sweis | |
| 2002/0007185 A1 | 1/2002 | Aghion | |
| 2003/0128324 A1 | 7/2003 | Woods | |
| 2008/0055541 A1* | 3/2008 | Coulter | G02C 7/101 351/159.45 |
| 2011/0075092 A1 | 3/2011 | Nordyke | |
| 2011/0310318 A1 | 12/2011 | Kawagoe | |
| 2012/0127382 A1 | 5/2012 | Hirakata | |
| 2012/0224260 A1 | 9/2012 | Healy | |
| 2012/0262451 A1 | 10/2012 | Kotani | |
| 2013/0194244 A1 | 8/2013 | Tamir | |
| 2013/0235286 A1 | 9/2013 | Hung | |
| 2014/0101812 A1 | 4/2014 | Richards | |
| 2016/0262467 A1 | 9/2016 | Magnusson | |
| 2017/0367891 A1* | 12/2017 | Magnusson | A61F 9/067 |

FOREIGN PATENT DOCUMENTS

| | | |
|---|---|---|
| WO | WO 2015-181340 | 12/2015 |
| WO | WO 2018-229688 | 12/2018 |

OTHER PUBLICATIONS

International Search Report for PCT International Application No. PCT/IB2020/054723, mailed on Jun. 19, 2020, 4 pages.

* cited by examiner

DARKENING FILTER COMPRISING A NON-UNIFORM PATTERN OF SWITCHABLE SHUTTERS

BACKGROUND

The present disclosure relates to darkening filters which are suitable for selectively darkening an optically transmissive window for protection from light, in particular from high intensity light. The present disclosure also relates to a method of operating such darkening filters. The present disclosure furthermore relates to vision-protective headgears, welding shields and panes comprising the darkening filters according to the present disclosure.

Automatic darkening filters are often provided on protective headgear, where protection from high intensity light is desired. Automatic darkening filters commonly have a switchable filter that automatically changes from a light-transmission-state to a dark-transmission-state in response to incident light. The switching is generally achieved through use of a photodetector that is located on, or as part of, personal protective equipment. The photodetector recognizes the presence of the incident light-to-be-filtered, and an electronic module generates a control voltage that, when applied to the switchable filter, causes the filter to change from the light-transmission-state to the dark-transmission-state. Automatic light filters have been designed which contain liquid-crystal cells located between polarizing films. U.S. Pat. No. 4,240,709 to Hornell describes a switchable filter that has a single-twisted, nematic, liquid-crystal cell sandwiched between a pair of mutually crossed polarizers. The liquid-crystal cells are generally flat, optically-transparent, glass substrates that include transparent electrode and alignment layers. The liquid-crystal molecules orientate themselves in a particular direction when a voltage is applied across the liquid-crystal cell under the control of an electronic module. Many commercially available products use this kind of switchable filter. The use of an automatic-darkening filter in a protective shield gives significant ergonomic benefits. Previously welders, for example, had to "nod" their welding shield down when they struck the welding arc to ensure that their eyes were protected from the torch light. Automatic welding filters eliminated this action since the welding shield could be continuously placed in the down position. As a result, weld pattern quality has been generally improved because more accurate electrode placement can be achieved. Productivity improvements also have been noted since grinding and rework have been correspondingly reduced.

Known welding filters have typically been set up with regular arrays of equidistantly arranged switchable shutters of the same size and shape. Such regular arrays of shutters may provide sufficient protection from light on the one hand, but may on the other hand switch an undesired large area of the filter to a dark state because of an inflexible arrangement of the array. This may lead to a possible limitation of the visibility of a user of such darkening filters.

Therefore, a need exists for a darkening filter to prevent unnecessary limitation of the user's or wearer's visibility when using a darkening filter for protection from light. Also, a need exists to improve the protection against glaring while maintaining good viewing conditions for the wearer or user.

SUMMARY

The present disclosure provides a darkening filter mounted in a forward-facing optically transmissive window. The filter comprises a pattern of switchable shutters that are each capable of being switched between at least a dark state and a light state. The filter further comprises a shutter control system that is connected to each shutter of the pattern of shutters so as to be able to control the switching of each of the shutters. The pattern of shutters is non-uniform. Such a non-uniform pattern is advantageous because a certain area of the darkening filter can be switched more flexible than with a uniform shutter pattern. Thus, the darkening filter according to the present disclosure provides for sufficient protection from light, in particular high intensity light, without impacting the viewing conditions of the wearer or user in an undesired or unnecessary way. A non-uniform pattern is understood to comprise switchable shutters of different size, i.e. some shutters may be larger and some may be smaller in cross-section. The size may vary along one or both longitudinal dimensions of the pattern. A gradient in size of the shutters may be formed by successively decreasing or increasing the shutter size along a dimension. Also, the non-uniform pattern may comprise shutters which are not equidistantly spaced, i.e. the distance from one to another shutter can vary along one or both longitudinal dimensions of the pattern. A gradient in distance of the shutters may be formed by successively decreasing or increasing the shutter distance along a dimension. Furthermore, the non-uniform pattern may comprise shutters of different shape. Also, groups of shutters may be formed so as to be switched at once, e.g. from a light state to a dark state of vice versa. Such grouping may help to reduce the numbers of individual shutters to be switched and may, for example, lead to a shorter switching time. Each of the individual shutters can switch between at least a light state (in which it is relatively highly light transmissive) and a dark state (in which it is relatively non-transmissive to light). In some embodiments, a shutter can also switch to at least one intermediate state that exhibits a light transmissivity in between of the light state and the dark state. In specific embodiments, a shutter can switch into any of a multiplicity of intermediate states between the light state and the dark state. The term state is meant as a condition of relative light transmissivity, or opacity, of a shutter of an automatic darkening filter.

The amount of incident light transmitted by a shutter in the various states can be characterized in various ways. One way commonly used in the art is the visible light transmission of the shutter. In various embodiments, a shutter is configured so as to exhibit a visible light transmission of less than about 0.5%, less than about 0.1%, or less than about 0.05%, when in a dark state; and, to exhibit a visible light transmission of greater than about 3%, greater than about 10%, greater than about 20%, or greater than about 50%, when in a light state. In various embodiments the visible light transmission of a shutter when in an intermediate state may be less than about 10%, less than about 5%, or less than about 2%, and may be greater than about 0.5%, greater than about 1%, or greater than about 1.5%. Other ranges are possible.

Typically, a switchable shutter comprises a first polarizer, a second polarizer, and a first liquid-crystal cell. The first polarizer has a first polarization direction, and the second polarizer has a second polarization direction. The second polarization direction may be the same or different from the first polarization direction. The liquid-crystal cell is disposed between the first and second polarizers. The liquid crystal cell contains first and second optically transparent, flexible, glass layers and has a liquid crystal layer located between the first and second, optically-transparent flexible glass layers. The first cell may be a twisted, nematic, liquid-crystal cell located (sandwiched) between the first and second polarization filters. As mentioned above, the polarization filters may have substantially orthogonal polarization directions, in which the polarization direction of the first polarization filter is oriented at approximately 90° to the polarization direction of the second polarization filter. These orthogonal polarization directions enable the cell to switch from a light state, and to maintain a light state, when no control voltage is applied to the cell; and to switch to a dark state and to maintain a dark state, when voltage is applied to the cell. More details of such shutters are, for example, described in WO 2018/229688 or US 2016/0262467.

The darkening filter according to the present disclosure comprises a shutter control system. The shutter control system is connected to the individual shutters of the non-uniform pattern of switchable shutters. The shutter control system is such connected to each shutter that the shutter control system can at least send control signals to individual shutters (i.e. by sending control signals to individual shutters of an array of shutters of a liquid-crystal cell, as discussed earlier herein) to assume any desired state (e.g., light, dark, intermediate, and so on). Two-way communication between the control system and the shutters is possible if desired; e.g. the shutters may be configured to send update or confirmation signals regarding the particular state of the shutters at any given time. The shutter control system can switch the shutters between various states by the use of any convenient control signal; for example, by varying voltages that are applied to the shutters. Upon a change in a control signal being applied by the shutter control system, a shutter may often exhibit a response time in lighter-to-darker transitions of less than one millisecond, and a response time in darker-to-lighter transitions of around a few milliseconds. When a constant value of a control signal is applied, a shutter typically exhibits a relatively constant light transmission.

In one embodiment, the darkening filter further comprises at least one image acquisition device, wherein the shutter control system is receivably connected to the image acquisition device. The shutter control system is configured to receive light intensity mapping information from the at least one image acquisition device and is configured to use the light intensity mapping information to choose states to which the shutters are switched. Such image acquisition device provides for a reliable and effective way of protecting a user or wearer from light without too much impact to the viewing conditions. By receivably connected is meant that the control system is configured to receive light intensity mapping information from the at least one image acquisition device. For example, the image acquisition device is oriented so that it faces forward, so that it can acquire an image that at least generally corresponds to the view that a wearer or user observes through the automatic darkening filter. Such a view may encompass not only any high-intensity light emission from a workpiece being worked on, it may also include other portions of the workpiece (that are not emitting high-intensity light), and a small or large background area surrounding the workpiece. It may be preferential to locate the image acquisition device in close proximity to the optically transmissive window of the darkening filter, so that the image acquisition device images an area that closely approximates the view visible through the automatic darkening filter. It will be understood that in ordinary use of the darkening filter, the image(s) that are acquired by the image acquisition device are not displayed for, and thus are not visible to, the person who is using the darkening filter. From this image of the view, a signal is generated (either directly by image acquisition device, or by any ancillary microprocessor or the like that is connected thereto) that carries mapping information representative of the area distribution of light intensity within the view. That is, each area of the view that is depicted in the image carries information regarding the intensity of light in that area, with e.g. areas of higher light intensity and areas of lower light intensity being present over the length and breadth of the view. The shutter control system is configured to receive this signal from image acquisition device (whether directly, or indirectly through some intermediary processor) and to use the information therein (along with eye position information, as discussed later herein) to determine an appropriate state to which to control various the individual shutters of the array of shutters. The image acquisition device is thus in communication with other components of the shutter control system via one or more connections (which may be a dedicated wire, an optical fiber, a wireless connection, etc.), as needed for functioning of the system.

The image acquisition device may be any suitable device (e.g., camera) that can acceptably acquire an image of the view. For example, it might comprise one or more CMOS image sensors, charge-coupled devices (CCDs), or the like, so that e.g. a digital image may be generated without the need to perform analog-to-digital conversion. The wavelength range over which a sensor is most sensitive to light may be chosen appropriately. In many embodiments, an array (e.g., a solid-state array) of such sensors may be used in combination to serve collectively as image acquisition device. In various embodiments, the image acquisition device may be configured to acquire images continuously, or intermittently. Similarly, the signals from the image acquisition device may be sent to the shutter control system continuously (e.g. as a continuous video stream), or intermittently. If intermittent monitoring and/or signal transmission is utilized, it is preferably done at sufficiently high frequency to enable sufficiently rapid response of a shutter.

In another embodiment, the darkening filter further comprises at least one eye position monitoring device. The shutter control system is receivably connected to the eye position monitoring device. The shutter control system is configured to receive light intensity mapping information and eye position information from the at least one eye position monitoring device and is configured to use the received information in combination to choose states to which the shutters are switched. Such a darkening filter provides for a reliable and effective way of protecting a user or wearer from light without too much impact to the viewing conditions, in particular the way of protection is further improved and the impact to the user's or wearer's view is further minimized because the system takes the eye positions into account. By receivably connected is meant that the shutter control system is configured to receive information from the eye position monitoring device that allows the position of at least the pupil, and in some cases the entire eye (eyeball) of a wearer of the headgear, to be established (calculated) in three dimensional space with respect to the headgear and specifically with respect to the automatic darkening filter present in the forward-facing optically transmissive window. For example, the eye position monitoring device is oriented so that it faces rearward toward an eye of the wearer of the darkening filter. In some embodiments a single eye position monitoring device (that is e.g. laterally centrally located) may be used to monitor the position of the right and left eyes of the wearer. However, in some embodiments it may be advantageous to provide a dedicated right eye position monitoring device and a dedicated left eye position monitoring device. Such an arrangement may provide that information can be obtained not only with regard to the vertical and lateral position of each pupil with respect to the automatic darkening filter but can also be used to map the front-rear (depth) distance of each pupil away from the automatic darkening filter. (It will be appreciated that, strictly speaking, information from each of the two monitoring devices may be used in combination to provide such information; however, such devices will be referred to for convenience as being right and left eye position monitoring devices.) Any suitable device that obtains information that enables the location of at least the pupil (and in some cases all exposed portions) of a user's eye to be determined at any given time, may be suitable for use as an eye position monitor. In some embodiments, such a device can comprise a rearward-facing image acquisition device that obtains an image of the eyeball of a user. At least two such devices may be optimally used, so that (e.g. if both devices obtain images that overlap enough to include at least one location in common) parallax methods (or any other suitable method) can be used to ascertain the front-rear distance of at least the pupil of each eye relative to the automatic darkening filter. Since the automatic darkening filter will be a macroscopically large entity that moreover may be curved rather than being planar, in some embodiments the position of at least each pupil can be ascertained with respect to one, two, three, or more reference locations somewhere on the headgear or on the automatic darkening filter. (In some embodiments, the locations of the eye position monitoring devices themselves may conveniently serve as reference locations.)

In a further embodiment, the non-uniform pattern of the darkening filter comprises shutters of different size. Such non-uniform pattern may be beneficial because shutters of different size may allow for a more flexible switching of the darkening filter while having less impact to the user's viewing conditions. In various embodiments, the individual shutters may each occupy at least about 0.1, 0.2, 0.5, 1.0, 2.0, 4.0, or 10.0 square millimeters of the automatic darkening filter. In further embodiments, the individual shutters may each occupy at most about 200, 100, 60, 40, 20, 10, or 5 square millimeters.

In yet a further embodiment, the non-uniform pattern of the darkening filter comprises shutters of different shape. Such non-uniform pattern may be beneficial because shutters of different shape may allow for a more flexible switching of the darkening filter while having less impact to the user's viewing conditions. The individual shutters may have any desired shape, e.g. at least generally rectangular (e.g. square), round, oval, triangular, pentagonal, hexagonal, octagonal or irregular.

In another embodiment, the non-uniform pattern of the darkening filter comprises shutters of different size and of different shape. For example, not all of the shutters of the non-uniform pattern are of the same size as well as of the same shape. It is understood, that one shutter can have a different shape and a different size compared to another shutter. Also, it is understood that a shutter may have the same size compared to another shutter, but having a different shape or vice versa. This might be beneficial because such a pattern provides for an increased flexibility for arranging the shutters in such a non-uniform pattern.

In one embodiment, the non-uniform pattern of the darkening filter is predetermined. For example, the positions and size of each of the switchable shutters are fixedly arranged and cannot be changed by the shutter control system. This may be beneficial because the construction is more robust and the system may have shorter reaction or set-up times. Also, such filter may be easy to manufacture and easy to control. In certain embodiments, the darkening filter with a predetermined pattern may also comprise a pattern which is adjustable. Also, groups of shutters may possibly be grouped so as to be switched from one state to another at once.

In another embodiment, the non-uniform pattern of the darkening filter is adjustable. For example, the positions of each of the switchable shutters may be varied by the shutter control system. In particular, the shutter control system may automatically adjust the pattern of switchable shutters. Adjusting the pattern is understood that the size of the shutters varies, the distance of the shutters to each other varies and/or that the shape of the shutters varies. This may be beneficial because the darkening filter can be adjusted to different condition of use and/or to different wearers of the darkening filter even during the use of the darkening filter. Alternatively, the adjustment of the pattern of switchable shutters may be done manually by a user or wearer of the darkening filter according to the specific demand or desire of the user or wearer. This may be beneficial as the darkening filter can be individualized by the user or wearer. In certain embodiments, the darkening filter with an adjustable pattern may also comprise a pattern which is predetermined.

In a further embodiment, the non-uniform pattern of the darkening filter comprises a first region having a first density of shutters per area and at least one second region having a second density of shutters per area. The density of shutters in the first region is higher than the density of shutters in the second region. This may be beneficial because the reaction time of the system is short with such a configuration and the impact to the user's or wearer's view is even further minimized, in particular if the first region with the higher density is arranged in the area of the most interest to the user or wearer of the darkening filter. The size of the shutters in the first region is not necessarily the same for all shutters of the first region, but it can vary even within the first region. Furthermore, the size of the shutters in the second region is not necessarily the same for all shutters of the first region, but it can vary even within the second region. The number of shutters may be high, almost infinitive.

In yet a further embodiment, the first region of the darkening filter is arranged in a main view focus of the filter. The main view focus represents an area of the darkening filter through which the user or wearer of the darkening filter can see, for example, a workpiece. This may be beneficial because the impact to the user's or wearer's view is even further minimized, if the first region with the higher density is arranged main view focus. Such a filter may be particularly useful if the filter is arranged close to the user's eyes.

In another embodiment, the filter comprises two first regions and wherein the two first regions are aligned with positions corresponding to the location of the eyes of a user. This may be beneficial because the impact to the user's or wearer's view is even further minimized if the first regions having a higher density of switchable shutters are associated to the eyes of a user or wearer. Such a darkening filter with two first regions may particularly be useful if an eye tracking is used.

In yet another embodiment and as already mentioned above, each of the shutters of the darkening filter is capable of being switched to at least one intermediate state. For example, such an intermediate state exhibits a light transmissivity in between of the light state and the dark state. In specific embodiments, a shutter can switch into any of a multiplicity of intermediate states between the light state and the dark state. The term state is meant as a condition of relative light transmissivity, or opacity, of a shutter of an automatic darkening filter. This may be beneficial because it may help to reduce the impact to the user's or wearer's view. Also, a finer degree of switching the shutter may be achieved with such intermediate states, to which the shutters may be switched. Furthermore, shutters which can be switched to an intermediate state may also provide for a smoother transition between a shutter in a dark state and a shutter in a light state, i.e. thereby avoiding sharp edges and thereby providing more natural viewing conditions.

In one embodiment, the shutter control system of the darkening filter is configured to use the light intensity mapping information and the eye position information in combination to identify a first set of shutters of the pattern of shutters as being positioned on a direct optical path between a source of light and at least a pupil of an eyeball of a user of the filter. The shutter control system is configured to selectively switch the first set of shutters from a light state to a dark state and to maintain them in the dark state. This may be beneficial because the shutters being on a direct optical path provide sufficient protection from light to the user or wearer. In certain embodiments, the first set of shutters is maintained in the dark state as long as the set of shutters is on this direct optical path, e. g. as long as the source of light continues to emit light and as long as the geometric relationship of the light source, the darkening filter and the user's or wearer's eyeball has not changed so as to shift the location of the direct optical path.

In another embodiment, the shutter control system of the darkening filter is further configured to use the light intensity mapping information and the eye position information in combination to identify a second set of shutters of the pattern of shutters as not being positioned on a direct optical path between a source of light and at least a pupil of an eyeball of the user of the darkening. This may be beneficial because by distinguishing a first set of shutters from other shutters, the system is capable of initiating different operations for different shutters, in particular maintaining some shutters in a light state, which helps to reduce the time for switching the shutters.

In yet another embodiment, the shutter control system of the darkening filter is configured to maintain at least some shutters of the second set of shutters in a light state and/or to switch at least some shutters of the second set of shutters to an intermediate state and to maintain them in the intermediate state. This may be beneficial because by identifying the second set of shutters, which may be switched to a different state than the first set of shutters, the viewing conditions of the user or wearer are maintained and are not too much impacted, respectively. Alternatively, the second set of shutters may not be switched at all. In this case, the time for switching may be reduced due to the lower number of shutters to be switched. The second set of shutters can, but does not necessarily need to, include all of the other shutters of the pattern, i.e. that are not part of the first set of shutters.

In a further embodiment, the first and second region(s) of the darkening filter of first and second densities of shutters are arranged such that the first region is being positioned on a direct optical path between a source of light and at least a pupil of an eyeball of a user of the darkening filter; and such that the second region is not being positioned on a direct optical path between a source of light and at least a pupil of an eyeball of a user of the darkening filter. This is beneficial because by arranging the first region with the higher density on the direct optical path a good protection from light is achieved which minimizing the impact to the user's or wearer's view in an undesired way. Alternatively, the first region can be positioned such that is not on a direct optical path and the second region can be positioned such that it is on a direct optical path. Such an arrangement would be beneficial, if the light source is not positioned in a direct optical path, for example if the light source in a welding operation is generated by another welder nearby or if the filter is used in a vehicle and the light source is not in a direct optical path.

In yet a further embodiment, the at least one eye position monitoring device of the darkening filter is configured to monitor the position of at least the pupil of a user's eyeball in relation to at least one reference location of the darkening filter. The eye position monitoring device is further configured to perform as an eye-tracking device that monitors a direction in which the user is gazing. Such a filter would be beneficial as it provides for a better adaption to specific user viewing conditions.

In one embodiment, the darkening filter is curved. For example, the darkening filter may be curved about one, two or three axes. In addition, the shutters may be curved as well, for example, about one, two or three axes. A curved arrangement of the darkening filter and/or the shutters is beneficial because such a shape may better fit with articles where the darkening filter is built into, for example, a vision-protective headgear, a welding shield or a welding helmet, a pane or the like having a curved shape itself.

The present disclosure also relates to a method of operating a darkening filter further comprises the steps of using light intensity mapping information and eye position information in combination to identify a first set of shutters of the pattern of shutters, which first set of shutters is positioned on a direct optical path between a source of light and at least a pupil of an eyeball of a user of the filter; using the light intensity mapping information and eye position information in combination to identify a second set of shutters of the pattern of shutters, which second set of shutters is not positioned on a direct optical path between a source of light and at least a pupil of an eyeball of the user of the filter; and, selectively switching the first set of shutters from a light state to a dark state, while maintaining at least some shutters of the second set of shutters in a light state. Such a method switching shutters in a non-uniform pattern is advantageous because a certain area of the darkening filter can be switched more flexible than with a uniform shutter pattern. Thus, the darkening filter according to the present disclosure provides for sufficient protection from light, in particular high intensity light, without impacting the viewing conditions of the wearer or user in an undesired or unnecessary way. In certain embodiments, each of the shutters is capable of being switched to at least one intermediate state. The darkening filter is mounted in a forward-facing optically transmissive window and comprises a pattern of switchable shutters that are each capable of being switched between at least a dark state and a light state. The filter further comprises a shutter control system that is controllably connected to each shutter of the pattern of shutters so as to be able to control the switching of each of the shutters. The pattern of shutters is non-uniform. Such a method switching shutters in a non-uniform pattern is advantageous because a certain area of the darkening filter can be switched more flexible than with a uniform shutter pattern. Thus, the darkening filter according to the present disclosure provides for sufficient protection from light, in particular high intensity light, without impacting the viewing conditions of the wearer or user in an undesired or unnecessary way. Also, such a method including switching shutters to an intermediate state provides for a smoother transition between a shutter in a dark state and a shutter in a light state, i.e. thereby avoiding sharp edges and thereby providing more natural viewing conditions.

The present disclosure also relates to a darkening filter is part of a vision-protective headgear. A vision-protective headgear comprising a darkening filter according to the present disclosure is beneficial because the darkening filter provides a good protection from light, which is particularly useful where such headgears are used. Typically, a vision-protective headgear comprises a main body and a suspension having a band for fixing the headgear. The darkening filter according to the present disclosure is typically mounted in a forward side of the headgear, i.e. in the direction of which the user or wearer is gazing into.

In another embodiment, the darkening filter is part of a welding shield. A welding shield comprising such a darkening filter is beneficial because the darkening filter provides a good protection from light, which is particularly useful where such welding shields are used. Typically, a welding shield comprises a main body and a suspension having a band for fixing the headgear. The darkening filter according to the present disclosure is typically mounted in a forward side of the headgear, i.e. in the direction of which the user or wearer is gazing into.

In a further embodiment, the darkening filter is part of a pane. The pane is part of a vehicle windscreen or a glazing of a building. A pane comprising a darkening filter according to the present disclosure is beneficial because the darkening filter provides a good protection from light, which is particularly useful where such panes are used.

The invention was described in various embodiments above. It is understood by a person skilled in the art, that one, several or all of the above-mentioned embodiments can be combined with each other.

BRIEF DESCRIPTION OF THE DRAWINGS

The disclosure will now be described in more detail with reference to the following Figures exemplifying particular embodiments of the disclosure.

DETAILED DESCRIPTION

Figure 1:
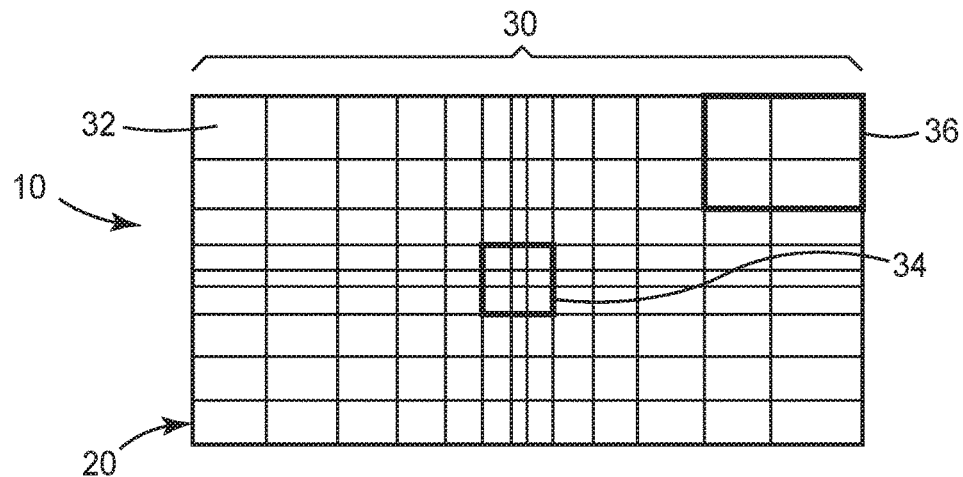
FIG. 1 is a schematic view of a darkening filter according to one embodiment of the present disclosure with all shutters being in a light state.
Figure 2:
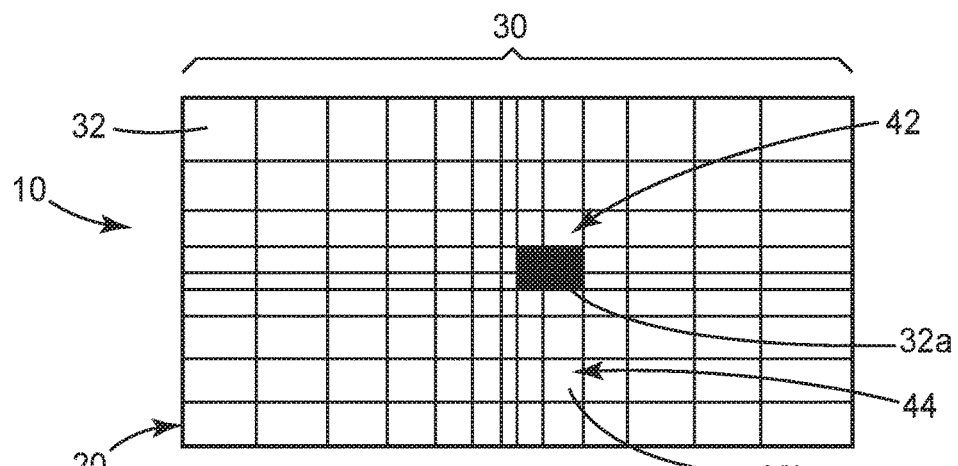
FIG. 2 is a schematic view of the darkening filter of FIG. 1, with some shutters are in a dark state.

A first embodiment of a darkening filter 10, which is mounted in a forward-facing optically transmissive window 20, according to this disclosure is schematically shown in FIG. 1. The darkening filter 10 comprises a pattern 30 of switchable shutters 32. As illustrated, the pattern 30 is non-uniform, i.e. the size of the shutters 32 vary along two dimensions of the pattern 30. As can be seen from FIG. 1, shutters of rather large size are arranged in outer regions of the darkening filter 10, see e.g. in second region 36, whereas shutters with rather small size are arranged towards the center region of the darkening filter 10, see e.g. in the first region 34. Between the rather large shutters and the rather small shutters, the size of the shutters successively decreases. The switchable shutters 32 can be switched between a light state (as illustrated for the shutters 32 in FIG. 1) and a dark state (not illustrated in FIG. 1). The shutters 32 being in a light state exhibit a relatively high light transmissivity, whereas the shutters 32 being in a dark state are relatively non-transmissive to light. In some embodiments, the shutters 30 can also be switched to an intermediate state (not illustrated in FIG. 1). FIG. 1 furthermore shows a first region 34 having a first density of shutters and a second region 36 having a second density of shutters. As apparent from FIG. 1, the size of the shutters 32 in the first region 34 is less than the size of the shutters 32 in the second region 36. The size of the shutters 32 in the first region 34 is not necessarily the same for all shutters 32 of the first region 34, but it can vary even within the first region 34. Furthermore, size of the shutters 32 in the second region 36 is not necessarily the same for all shutters 32 of the first region 36, but it can vary even within the first region 36. In the embodiment shown, the position of the first region 34 is centered within the pattern 30. Alternatively, the position of the first region 34 can be different and/or more than one first regions 34 can be arranged. For example, two first regions 34 can be arranged (see FIG. 7). FIG. 2 shows the darkening filter 10, which is mounted in a forward-facing optically transmissive window 20, of the embodiment as shown in FIG. 1 with the pattern 30, where some shutters 32a of the pattern 30 have been switched to the dark state, shown as dark squares indicated by 42 in FIG. 2. The shutters 32a switched to the dark state are in or proximate to the first region 34 as indicated in FIG. 1, but not shown here. The shutters 32a may also be outside of the first region 34, e.g. they may belong to the second region 36, which is not indicated in FIG. 2. Some other shutters 32b of the pattern 30 are switched to the light state, shown as white squares as indicated by 44. The shutters 32b, which are switched to the light state, may be in or proximate the second region 36 as indicated in FIG. 1, but not shown here. The shutter 32b may also be outside of the second region 36, which is not indicated in FIG. 2. Although only a few shutters 32a of the pattern 30 are indicated in FIG. 2 as switched to the dark state, further of the shutters 32 may be switched to the dark state as well and simultaneously, respectively. As described above, in response to incident light (not shown here) to the darkening filter 10, the shutter control system (not shown) switches the shutters either to a dark state, an intermediate state or to a light state (or maintains the shutters in one of these states).

Figure 3:
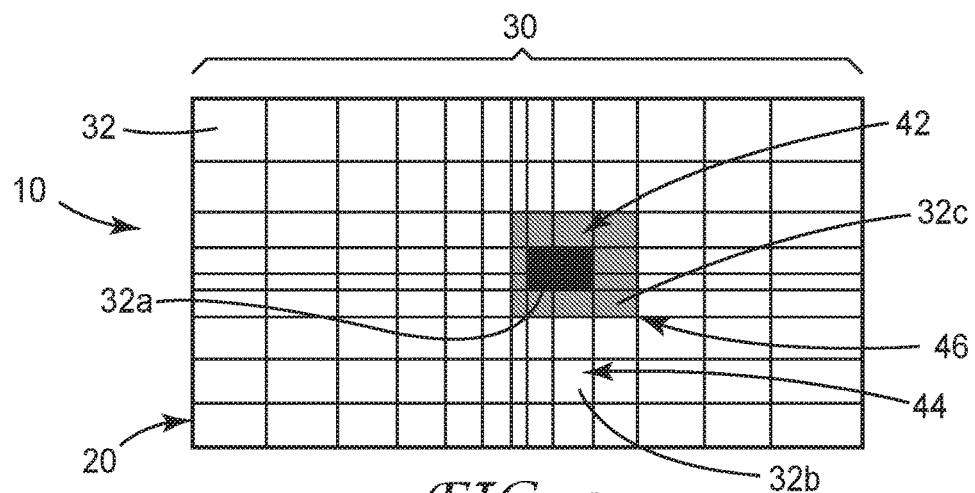
FIG. 3 is a schematic view of the darkening filter of FIG. 2, with in addition to shutters being in a dark state some shutters being in an intermediate state.

FIG. 3 shows the embodiment of the darkening filter 10, which is mounted in a forward-facing optically transmissive window 20, as shown in FIGS. 1 and 2. Here, in addition to the shutters 32*a* switched to the dark state and to shutters 32*b* switched to the light state, some shutters 32*c* are switched to an intermediate state, which are shown as grey squares as indicated with 46. The shutters 32*c* being in an intermediate state exhibit a light transmissivity in between of the light state and the dark state. As described above, in response to the incident light (not shown here) to the darkening filter 10, the shutter control system (not shown) switches the shutters either to a dark state, an intermediate state or to a light state (or maintains the shutters in one of these states).

Figure 4:
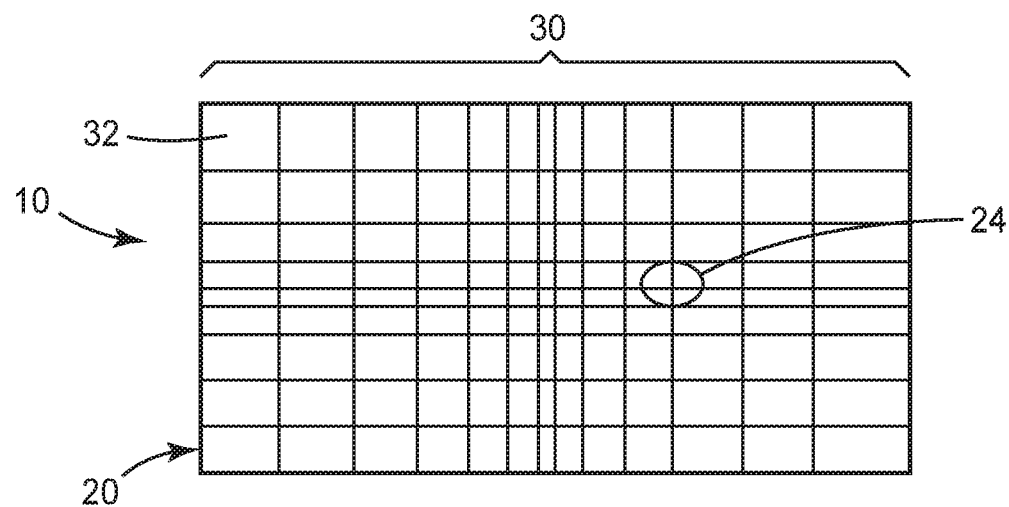
FIG. 4 is a schematic view of the darkening filter of FIG. 1 showing a light of high intensity.

FIG. 4 shows the darkening filter 10, which is mounted in a forward-facing optically transmissive window 20, as shown in FIG. 1 with the pattern 30 of switchable shutters 32. In addition, FIG. 4 shows an area of the darkening filter through which light from a light source 22 would be visible, indicated by 24. In the scenario as shown in FIG. 4, all shutters 32 are in a light state.

Figure 5:
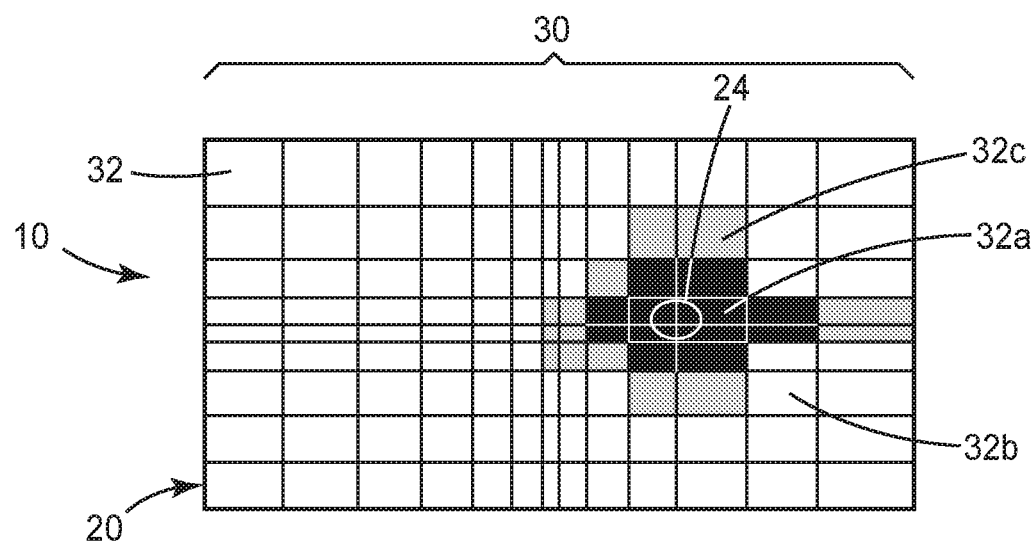
FIG. 5 is a schematic view of the darkening filter of FIG. 4, with some shutters being in a dark state and some other shutters being in an intermediate state.

FIG. 5 shows the darkening filter 10, which is mounted in a forward-facing optically transmissive window 20, as shown in FIG. 4 including the area where light from a light source 22 (not shown here) would be visible, indicated by 24. In addition, FIG. 5 indicates that some shutters 32*a* of the pattern 30 are switched to a dark state, some shutters 32*c* are switched to an intermediate state, while some shutters 32*b* are not switched, i.e. remain in a light state. This is in response to the light impacting on the darkening filter 10 being emitted from the light source, not shown in FIG. 5. As can be seen from FIG. 5, the center of the area covered by the switched shutters 32*a*, 32*c* is covered by shutters 32*a* switched to a dark state, whereas the shutters 32*c* surrounding the shutters 32*a* switched to a dark state are switched to an intermediate state. As described above, in response to the incident light to the darkening filter 10, the shutter control system (not shown) switches the shutters 32*a*, 32*b*, 32*c* either to a dark state, an intermediate state or to a light state (or maintains the shutters in one of these states).

Figure 6:
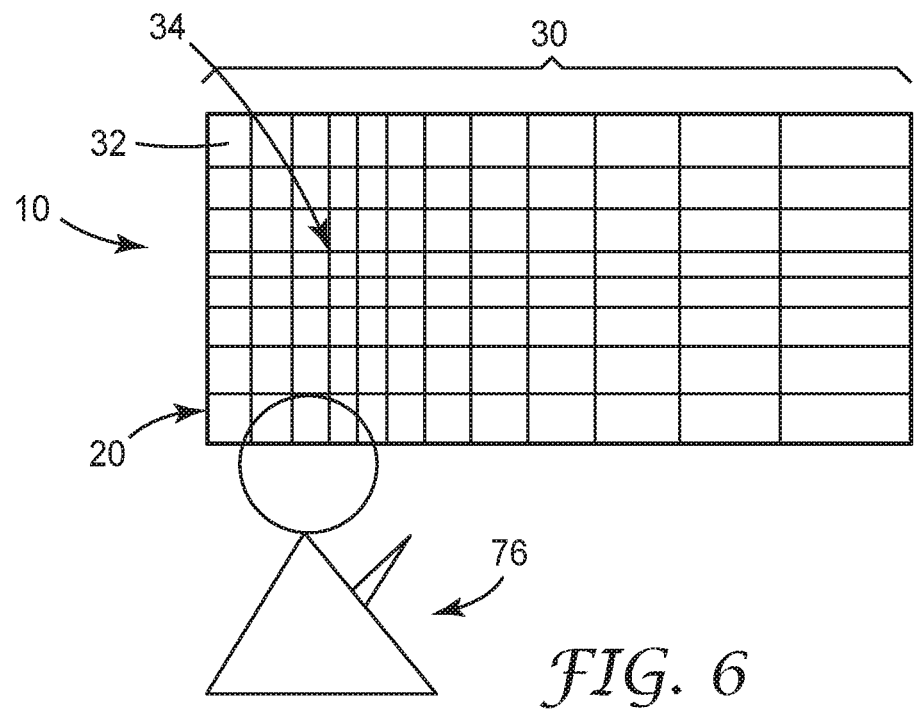
FIG. 6 is a schematic view of a darkening filter according to another embodiment of the present disclosure.

FIG. 6 shown an embodiment of the darkening filer 10, which is mounted in a forward-facing optically transmissive window 20, being different to the embodiment as shown in FIG. 1. Here, the first region 34 having a first density of shutters 32 is shifted from the center of the pattern 30 as shown in FIG. 1 to the left side. In addition, FIG. 6 shows a user or wearer 76 of the darkening filter. The first region 34 is aligned with the position of a user or wearer 76 and thus corresponds to the location of the eyes (not shown here) of the user or wearer 76.

Figure 7:
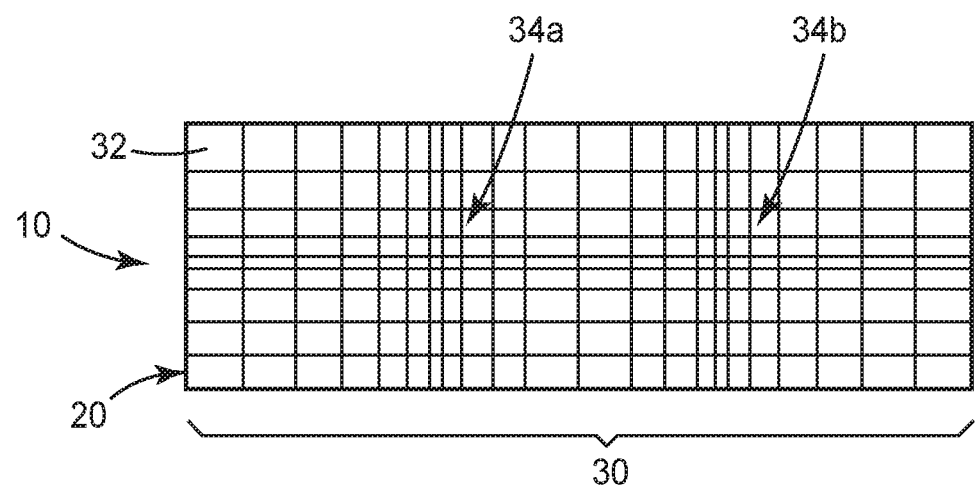
FIG. 7 is a schematic view of a darkening filter according to a further embodiment of the present disclosure.

FIG. 7 shows an embodiment of the darkening filter 10, which is mounted in a forward-facing optically transmissive window 20, with a pattern 30 of shutters 32 having two first regions 34*a*, 34*b*. The two first regions are each shifted to the left and to the right side, respectively, compared to the first region 34 as shown in FIG. 1. The two first regions 34*a*, 34*b* thereby form a left first region 34*a* and a right first region 34*b*. The two first regions 34*a*, 34*b* are aligned with positions corresponding to the location of the eyes of a user or wearer 76, both not shown in FIG. 7.

Figure 8:
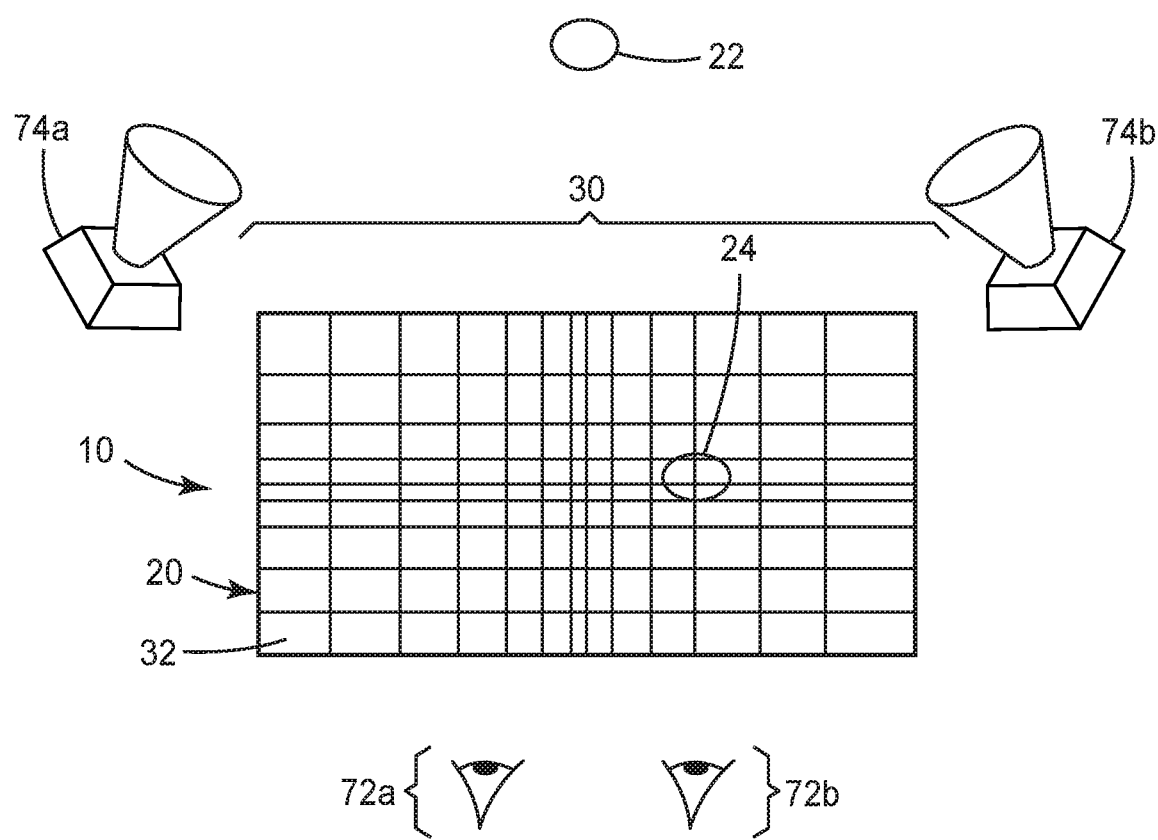
FIG. 8 is a schematic view of a darkening filter and an image acquisition device according to one embodiment of the present disclosure and the eyes of a user.

FIG. 8 shows the darkening filter 10, which is mounted in a forward-facing optically transmissive window 20, with the pattern 30 of switchable shutters 32 as shown in FIG. 4, where a light source 22 is shown which emits light resulting in light visible on the darkening filter 10 as indicated by 24. In addition, FIG. 8 shows two optical detectors 74*a*, 74*b*, e.g. cameras 74*a*, 74*b*. The cameras 74*a*, 74*b* are arranged such that one camera 74*a* is located on the left side of the darkening filter 10 and one camera 74*b* is located on the right side of the darkening filter 10. FIG. 8 furthermore shows the eyes 72*a*, 72*b* of a user or wearer 76, whereby the user or wearer 76 as such is not shown here. The cameras 74*a*, 74*b* are part of an image acquisition device, which is not shown in FIG. 8. The image acquisition device receives light from a light source 22 and compiles light intensity mapping information based on the received light. The shutter control system (not shown here) is receivable connected to the image acquisition device and receives the light intensity mapping information from there. Based on the light intensity mapping information, the shutter control system chooses the shutters 32 and the state to which these shutters 32 are switched, e.g. dark state, light state or intermediate state. The shutter control system may based on the received light intensity mapping information maintain some of the shutters 32 in a state where these have been in before. In the embodiment shown in FIG. 8, the shutters surrounding the area as indicated by 24 would be switched to a dark state in response to the light emitted from the light source 22.

Figure 9:
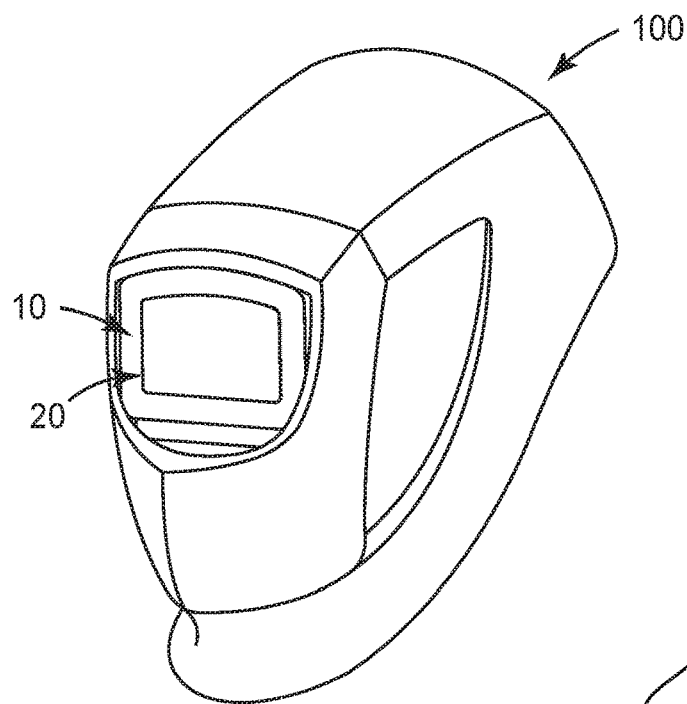
FIG. 9 is a perspective view of a welding helmet having a darkening filter according to an embodiment of the present disclosure.

FIG. 9 shows in a front-side perspective view of a vision-protective headgear 100 comprising the darkening filter 10, which is mounted in a forward-facing optically transmissive window 20, according to the present disclosure. In this embodiment, the darkening filter 10 is mounted in an opening in the headgear body. As can be seen from FIG. 9, the darkening filter 10 is flat. Alternatively, the darkening filter 10 may be curved, see FIG. 10 for more details. The headgear 100 may include a crown member (not shown) that engages the user's or wearer's head when the headgear is being donned.

Figure 10:
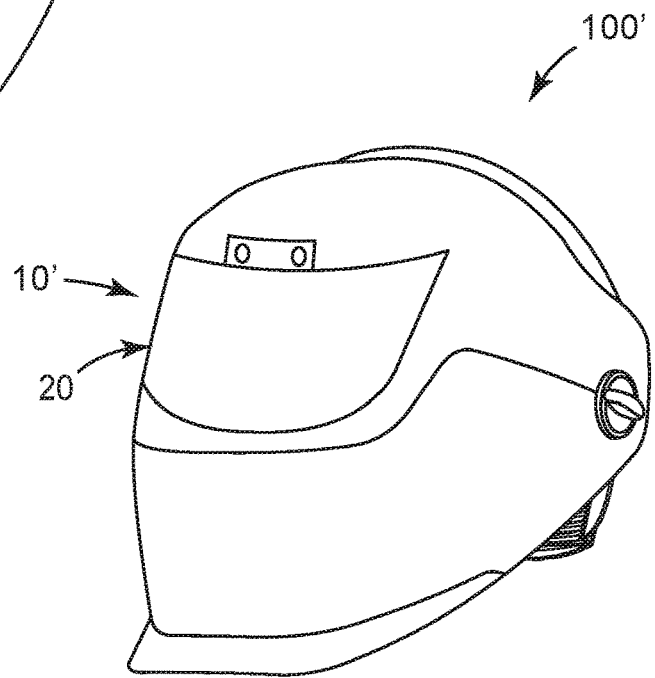
FIG. 10 is a perspective view of a welding helmet having a darkening filter according to an embodiment of the present disclosure.

FIG. 10 shows in a front-side perspective view a welding helmet 100' comprising the darkening filter 10', which is mounted in a forward-facing optically transmissive window 20, according to the present disclosure. In this embodiment, the darkening filter (10) is mounted in an opening in the welding helmet (100'). As can be seen in FIG. 10, the darkening filter 10' is curved. Typically, a welding helmet 100' comprises a main body and a suspension having a band for fixing the headgear. The darkening filter according to the present disclosure is typically mounted in a forward side of the headgear, i.e. in the direction of which the user or wearer is gazing into.

Figure 11:
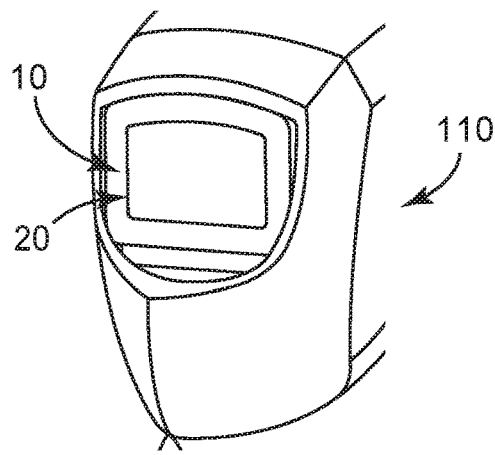
FIG. 11 is a perspective view of a welding shield having a darkening filter according to an embodiment of the present disclosure.

FIG. 11 shows in a front-side perspective view a welding shield 110 comprising the darkening filter 10, which is mounted in a forward-facing optically transmissive window 20, according to the present disclosure. In this embodiment, the darkening filter 10 is mounted in an opening in the welding shield body. As can be seen from FIG. 11, the darkening filter 10 is flat. Alternatively, the darkening filter 10 may be curved, see FIG. 10 for more details.

Figure 12:
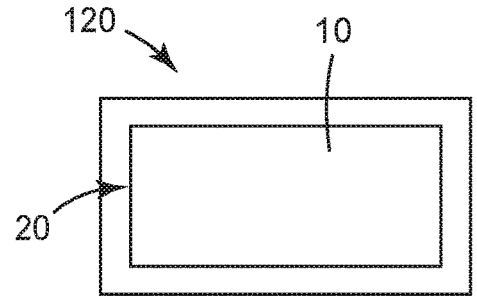
FIG. 12 is a top view of a pane having a darkening filter according to an embodiment of the present disclosure.

FIG. 12 shows in a top view a pane 120 comprising the darkening filter 10, which is mounted in a forward-facing optically transmissive window 20, according to the present disclosure. In this embodiment, the darkening filter 10 is mounted in an opening in the welding shield body. As can be seen from FIG. 11, the darkening filter 10 is flat. Alternatively, the darkening filter 10 may be curved, see FIG. 10 for more details. The pane 120 may be part of a vehicle windscreen or a glazing of a building (both not shown in FIG. 12).

Figure 13:
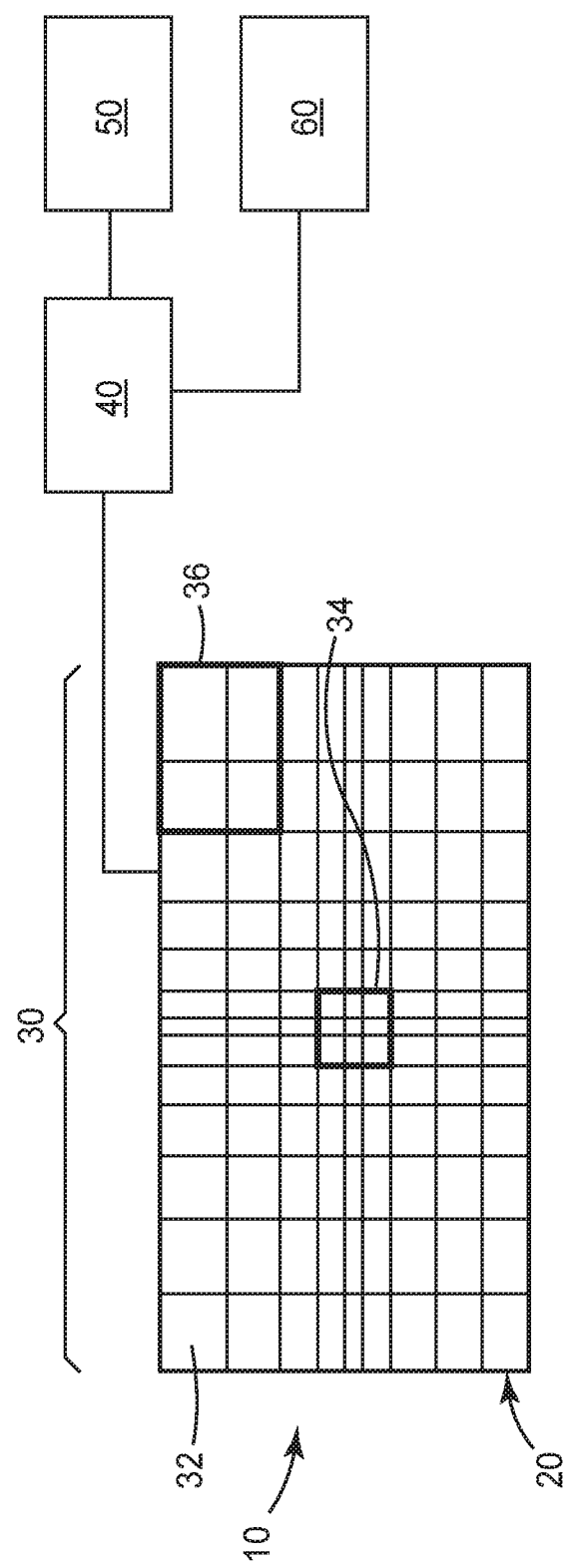
FIG. 13 shows in a schematic view a block diagram of one embodiment of a darkening filter according to the present disclosure.

FIG. 13 shows a block diagram of the darkening filter 10 according to one embodiment of the present disclosure. As can be seen, darkening filter 10 is mounted in a forward-facing optically transmissive window 20 and comprises a pattern 30 of switchable shutters 32, which can be switched between a dark state, a light state and one or more intermediate states. The darkening filter 10 further comprises a shutter control system 40, which is connected to each shutter 32 of the pattern 30 so as to be able to control the switching of each of the shutters 32. As can be seen, the pattern 30 is non-uniform. In the embodiment of FIG. 13, the darkening filter 10 moreover comprises an image acquisition device 50, wherein the shutter control system 40 is receivably connected to the image acquisition device 50. The shutter control system 40 is configured to receive light intensity mapping information from the image acquisition device 50 and is configured to use the light intensity mapping information to choose states to which the shutters 32 are switched. In the embodiment shown here, the darkening filter 10 moreover comprises an eye position monitoring device 60, wherein the shutter control system 40 is receivably connected to the eye position monitoring device 60. The shutter control system 40 is configured to receive light intensity mapping information from the image acquisition device 50 and eye position information from the eye position monitoring device 60 and is configured to use the received information in combination to choose states to which the shutters 32 are switched.

The invention claimed is:

1. A darkening filter mounted in a forward-facing optically transmissive window, the filter comprises
 a pattern of switchable shutters that are each capable of being switched between at least a dark state and a light state, and
 a shutter control system that is connected to each shutter of the pattern of shutters so as to be able to control the switching of each of the shutters, wherein
 the pattern of shutters is a predetermined non-uniform pattern, wherein the filter further comprises at least one image acquisition device, wherein the shutter control system is receivably connected to the image acquisition device and wherein the shutter control system is configured to receive light intensity mapping information from the at least one image acquisition device, wherein the filter further comprises at least one eye position monitoring device, wherein the shutter control system is receivably connected to the eye position monitoring device and wherein the shutter control system is configured to receive eye position information from the at least one eye position monitoring device, and is configured to use the received light intensity mapping information and eye position information in combination to choose states to which the shutters are switched.

2. The darkening filter according to claim 1, wherein the predetermined non-uniform pattern comprises shutters of different size and/or wherein the predetermined non-uniform pattern comprises shutters of different shape.

3. The darkening filter according to claim 1, wherein the predetermined non-uniform pattern comprises a first region having a first density of shutters per area and at least one second region having a second density of shutters per area and wherein the density of the shutters in the first region is higher than the density of the shutters in the second region.

4. The darkening filter according to claim 3, wherein the first region is arranged in a main view focus of the filter.

5. The darkening filter according to claim 3, wherein the filter comprises two first regions and wherein the two first regions are aligned with positions corresponding to the location of the eyes of a user.

6. The darkening filter according to claim 1, wherein the shutter control system is configured to use the light intensity mapping information and the eye position information in combination to identify a first set of shutters of the pattern of shutters as being positioned on a direct optical path between a source of light and at least a pupil of an eyeball of a user of the filter and wherein the shutter control system is configured to selectively switch the first set of shutters from a light state to a dark state and to maintain them in the dark state.

7. The darkening filter according to claim 6, wherein the shutter control system is further configured to use the light intensity mapping information and the eye position information in combination to identify a second set of shutters of the pattern of shutters as not being positioned on a direct optical path between a source of light and at least a pupil of an eyeball of the user of the darkening.

8. The darkening filter according to claim 7, wherein the shutter control system is configured to maintain at least some shutters of the second set of shutters in a light state and/or to switch at least some shutters of the second set of shutters to an intermediate state and to maintain them in the intermediate state.

9. The darkening filter according to any of claim 3, wherein the first and second region(s) of first and second densities of shutters are arranged such that the first region is being positioned on a direct optical path between a source of light and at least a pupil of an eyeball of a user of the darkening filter; and such that the second region is not being positioned on a direct optical path between a source of light and at least a pupil of an eyeball of a user of the darkening filter.

10. Method of operating a darkening filter according to claim 1, the method comprising the steps of:
 using light intensity mapping information and eye position information in combination to identify a first set of shutters of the pattern of shutters, which first set of shutters is positioned on a direct optical path between a source of light and at least a pupil of an eyeball of a user of the filter;
 using the light intensity mapping information and eye position information in combination to identify a second set of shutters of the pattern of shutters, which second set of shutters is not positioned on a direct optical path between a source of light and at least a pupil of an eyeball of the user of the filter; and,
 selectively switching the first set of shutters from a light state to a dark state and maintaining them in the dark state, while maintaining at least some shutters of the second set of shutters in a light state.

11. An apparatus comprising the darkening filter of claim 1, wherein the apparatus is one of: a vision-protective headgear, a welding shield, a pane of a vehicle windscreen, or a pane of a glazing of a building.

* * * * *